United States Patent [19]

Yokono et al.

[11] Patent Number: 5,221,474
[45] Date of Patent: Jun. 22, 1993

[54] TRANSFUSION FILTERING DEVICE

[75] Inventors: Osamu Yokono; Shinsuke Yokomachi, both of Fujinomiya, Japan

[73] Assignee: Terumo Kabushiki Kaisha, Tokyo, Japan

[21] Appl. No.: 813,360

[22] Filed: Dec. 24, 1991

[30] Foreign Application Priority Data

Dec. 28, 1990 [JP] Japan .................................. 2-418737

[51] Int. Cl.⁵ ............................................ B01D 19/00
[52] U.S. Cl. ...................................... 210/436; 55/158; 210/500.23; 604/406
[58] Field of Search ........................... 55/16, 158, 159; 210/927, 500.23, 436, 446; 604/406

[56] References Cited

U.S. PATENT DOCUMENTS 4,695,382 9/1987 Croni .
4,828,587 4/1989 Baurmeister et al. .

FOREIGN PATENT DOCUMENTS 0254100 1/1988 Fed. Rep. of Germany .
1-17383 3/1989 Japan .
WO87/02906 5/1987 World Int. Prop. O. .
WO90/11812 10/1990 World Int. Prop. O. .

Primary Examiner—Frank Sever
Attorney, Agent, or Firm—Frishauf, Holtz, Goodman & Woodward

[57] ABSTRACT

A transfusion filtering device for preventing foreign matters from entering into a human body. This transfusion fiber comprises a cylindrical housing, hydrophilic porous hollow fibers disposed in the housing in parallel with the axis of the housing, and hydrophobic porous hollow fibers disposed in the housing along the inner wall of the housing, the upper ends of the hydrophobic porous hollow fibers being exposed to the outer atmosphere so as to discharge air accumulated in the housing.

11 Claims, 4 Drawing Sheets

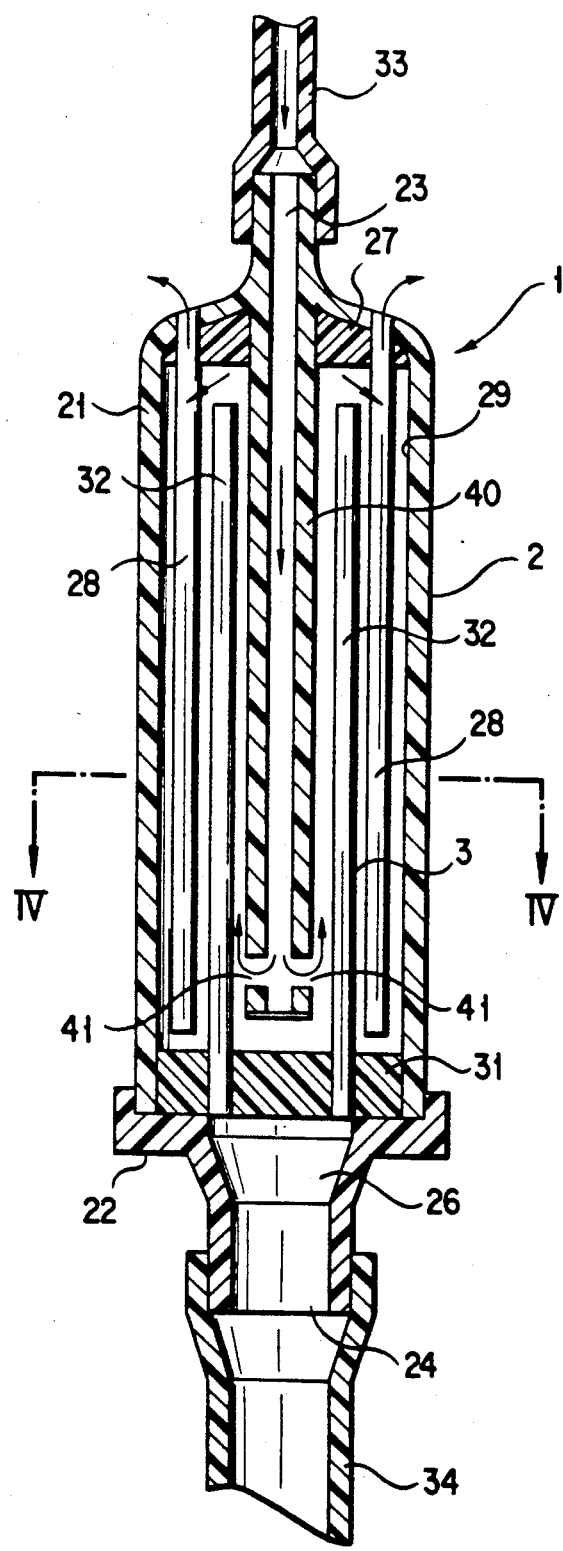
F I G. 4

TRANSFUSION FILTERING DEVICE

BACKGROUND OF THE INVENTION

1. Field of the Invention

The present invention relates to a transfusion filtering device for preventing infection caused by bacteria in blood transfusion and for preventing foreign materials from entering a human body.

2. Description of the Prior Art

A large amount of a transfusing liquid is injected into a patient in many medical treatments. It is necessary to use a transfusion filtering device in order to prevent infection caused by bacteria and to prevent foreign materials from entering the human body in injecting a transfusing liquid into a patient. The conventional transfusion filtering portion is defective in that, if an air stays in the filtering portion, the area of the filtering section capable of performing the filtering function is diminished, leading to a low filtering capability. For overcoming the difficulty, a transfusion filtering device provided with an air-releasing port is proposed in, for example, Japanese Published Examined Patent Application No. 1-17383.

The transfusion filtering device provided with an air-releasing port is constructed such that an air stays within the filter under a predetermined posture of the filter. The air-releasing port is formed in the air-staying portion of the filter. It follows that the transfusion filtering device noted above is defective in that a sufficient air-releasing effect cannot be obtained if the filter is used in another optional posture.

It should also be noted that the filtering section is planar in the conventional transfusion filtering device, making the filter bulky. In other words, it is difficult to miniaturize the transfusion filtering device while maintaining a high filtering capacity.

What should also be noted is that, in actually using a transfusion filtering device, it is necessary to fill the transfusion filtering device with a transfusing liquid and, at the same time, to perform a priming operation (air releasing operation) in order to remove bubbles remaining within the filter. To be more specific, it is necessary to release the remaining bubbles by, for example, turning the transfusion filtering device filled with a transfusing liquid upside down or by striking with fingers the filter filled with the transfusing liquid.

SUMMARY OF THE INVENTION

An object of the present invention is to provide a compact transfusion filtering device which permits overcoming the above-noted defects inherent in the prior art, which can be operated smoothly and efficiently, and which exhibits a sufficiently high filtering capability, said filter comprising a filtering portion and an air releasing section each formed of hollow fibers.

According to the present invention, there is provided a transfusion filtering device, comprising a housing provided with an inlet port of a transfusing liquid and an outlet port of a transfusing liquid, and a filtering portion formed within said housing and positioned between said inlet port and outlet port, wherein said filtering portion is provided with hydrophilic porous hollow fibers, and hydrophobic porous hollow fibers communicating with the outside are disposed within the housing extending from a portion around the transfusing liquid inlet port into the housing.

The housing may be substantially of a cylindrical shape, and the hydrophobic porous hollow fibers may be arranged a predetermined distance apart from each other along the inner wall of the housing. In this case, the hydrophilic porous hollow fibers are arranged in the central portion of the housing in the axial direction.

In the transfusion filtering device of the present invention constructed as described above, a transfusing liquid flows into the housing through the transfusing liquid inlet port provided at or near the upper end of the housing and further flows through the filtering section so as to come out of the filter through the transfusing liquid outlet port provided at or near the lower end of the housing. When passing through the hydrophilic hollow fibers forming the filtering section, the transfusing liquid is filtered by micro pores of the hydrophilic hollow fibers. The bacteria or the like contained in the transfusing liquid introduced into the filter are prevented by the micro pores of the hollow fibers from coming out of the filter. Likewise, the air bubbles within the housing are discharged to the outside through the hydrophobic porous hollow fibers. Since the hollow fibers are provided with hydrophobic micro pores, the transfusing liquid does not leak to the outside together with the air bubbles through the hydrophobic porous hollow fibers.

Suppose the posture of the transfusion filtering device is altered optionally. What should be noted is that the air bubbles within the housing are positioned in contact with the inner wall of the housing no matter how the posture of the filter may be altered. It follows that, if the hydrophobic porous hollow fibers are arranged a predetermined distance apart from each other along the inner wall of the housing, the air bubbles are brought into contact with the hollow fibers regardless of the posture of the transfusion filtering device so as to ensure the discharge of the air bubbles.

On the other hand, the hydrophilic porous hollow fibers are arranged in the central portion of the housing in the axial direction of the housing. Naturally, the hydrophilic hollow fibers are less likely to contact the air bubbles staying within the housing. As a result, the contact area between the filtering plane of the hydrophilic fibers and the transfusion liquid is not substantially diminished and, thus, the filtering efficiency is not substantially lowered.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4 is a vertical cross sectional view showing another embodiment of the present invention.

DETAILED DESCRIPTION OF THE PREFERRED EMBODIMENTS

Figure 1:
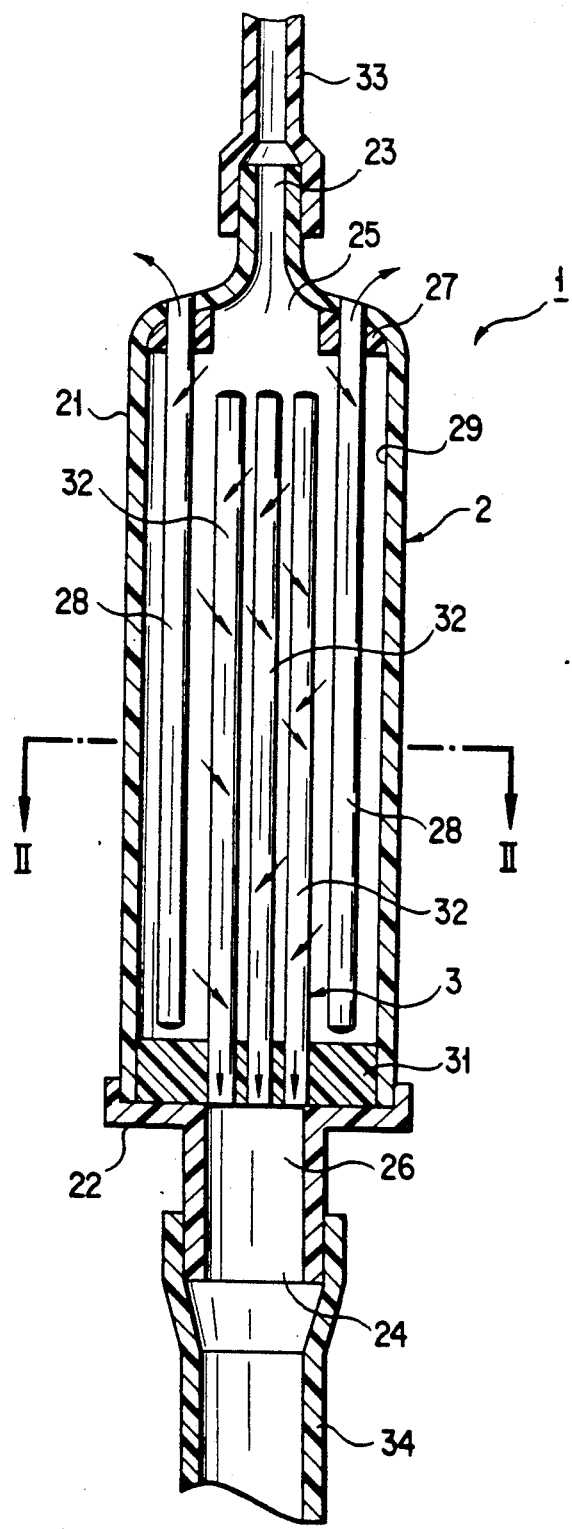
FIG. 1 is a vertical cross sectional view showing a transfusion filtering device according to one embodiment of the present invention.

The accompanying drawings collectively show a transfusion filtering device according to a preferred embodiment of the present invention. As seen from the drawings, a transfusion filtering device 1 of the present invention comprises a substantially cylindrical housing 2 consisting of a substantially cylindrical housing body 21 open at one end and a lid 22 closing the open end of the housing body 21. The housing body 21 is provided at the other end with a transfusing liquid inlet port 23. Also, the lid 22 is provided with a transfusing liquid outlet port 24. These inlet port 23 and the outlet port 24 project outward and are connected to pipes 33 and 34, respectively. The inlet port 23 is formed at or near the upper end of the housing 2, and the outlet port 24 is formed at or near the lower end of the housing 2.

Each of the housing body 21 and the lid 22 is formed of, for example, a polycarbonate resin, an acrylonitrile-butadiene-styrene terpolymer, a nylon resin, an acrylonitrile-styrene copolymer, a polymethyl methacrylate resin, a polystyrene resin, or a butadiene-styrene copolymer. It is also possible to use soft resins such as a vinylchloride resin and an ethylene-vinyl acetate copolymer. Where the housing body and the lid are formed of a soft material, it is possible to suppress a feeling of physical disorder when the transfusing filter is fixed to a human body.

A filtering portion 3 is formed in the open portion near the lid 22 of the housing body 21 so as to divide the liquid chamber within the housing 2 into a first chamber 25 on the side of the transfusing liquid inlet port 23 and a second chamber 26 on the side of the transfusing liquid outlet port 24. The filtering portion 3 consists of a sealing member 31 and a bundle of hydrophilic hollow fibers 32 fixed within the housing body in a manner to extend through the sealing member 31. The sealing member 31 acts as a barrier wall serving to seal the open end portion of the housing body 21 and to substantially partition the liquid chamber within the housing body 21. The sealing member 31 can be formed of, for example, an epoxy resin or a polyurethane resin.

Figure 2:
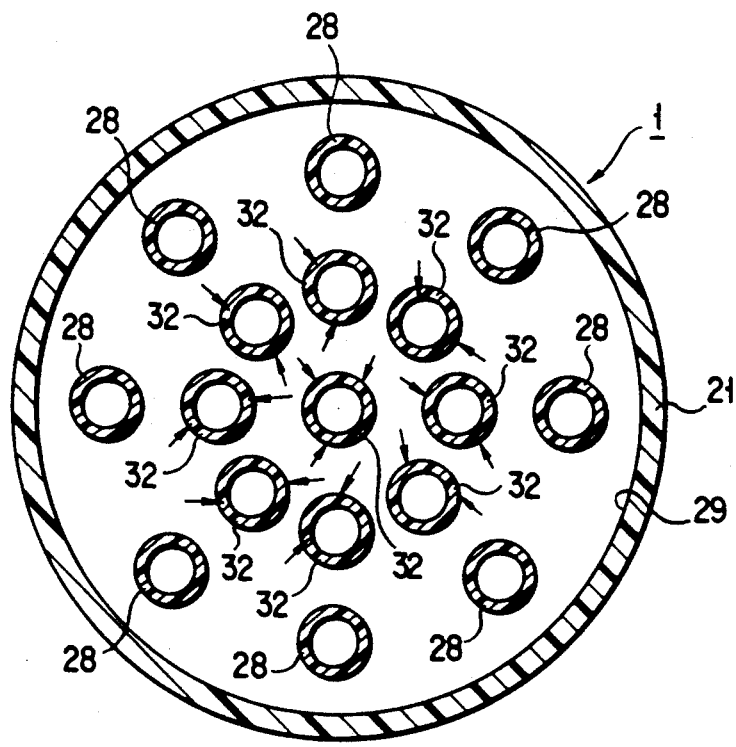
FIG. 2 is a cross sectional view along the line II—II shown in FIG. 1.
Figure 3:
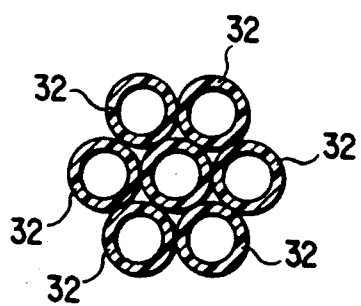
FIG. 3 is a cross sectional view exemplifying how hollow fibers are bundled in the present invention.

As shown in FIG. 2, a hydrophilic hollow fiber 32 is disposed substantially along the axis of the housing body 21. Further, eight hydrophilic hollow fibers 32 are equidistantly disposed in a circular arrangement to surround the central hollow fiber 32. In the embodiment shown in the drawings, the hydrophilic hollow fibers 32 are disposed separately from each other. However, it is also possible to use a bundle of about 2 to 20 hollow fibers 32 as shown in FIG. 3 in place of the individual hollow fibers 32 shown in FIG. 2. The hollow fiber 32, which is hydrophilic and porous, is sealed at the distal end and is open at the proximal end on the opposite side of the sealing member 31. Alternatively, the hollow fiber may be bent in a U-shape and fixed to the sealing member 3 such that the both ends of the U-shaped hollow fiber are aligned.

The hydrophilic porous hollow fiber is formed of, for example, a polysulfone resin, cellulose acetate, nitrocellulose, nylon, polypropylene subjected to a hydrophilic treatment, and polyethylene subjected to a hydrophilic treatment. A large number of micro pores formed on the surface of the porous hollow fiber are sized smaller than bacteria. As a result, the bacteria are removed from the transfusing liquid by the filtering function performed by the porous hollow fiber. To be more specific, the surface of the porous hollow fiber should have a porosity of about 30 to 90%, preferably about 60 to 85%. Also, the pore diameter should be about 0.01 to 0.45 micron, preferably about 0.1 to 0.3 micron. If a plurality of porous hollow fibers 32 having a small diameter are bundled together, the surface areas of the fibers are increased, leading to a marked improvement in the filtering capacity of the transfusion filter. In general, the outer diameter of the porous hollow fiber 32 may be in the range of from 0.1 mm to 1.5 mm, and the wall thickness thereof may range from 10 $\mu$m to 200 $\mu$m.

A thick wall portion 27 is circumferentially formed in the upper end portion of the housing body 21 in a manner to surround the transfusing liquid inlet port 23. Hollow fibers 28 extend through and are supported by the thick wall portion 27. The hollow fibers 28, which are hydrophobic and porous, are positioned within the first chamber 25 of the housing body 21 and equidistantly arranged along the inner wall 29 of the housing body 21. These hollow fibers 28 are sealed at the distal ends, extend to reach a region near the sealing member 31, and are arranged over substantially the entire region of the inner wall 29 within the first chamber 25. It should be noted that the hydrophobic hollow fibers 28 may not necessarily be extended down to the sealing member 31 as shown in FIG. 1, but may be slightly extended as for as a sufficient degassing is assured. In short, there is no restriction as to the length of the hollow fibers 28. On the other hand, the proximal ends of these hollow fibers 28 communicate with the outside of the housing body 21. As described previously in conjunction with the hydrophilic hollow fibers 32, the hydrophobic hollow fiber 28 may be of U-shape such that both ends of the hollow fiber 28 are aligned and fixed to the thick wall portion 27. In this case, both ends of the hollow fiber 28 are open and communicate with the outside of the housing body 21. Further, a plurality of hydrophobic hollow fibers 28 may be bundled together like the hydrophilic hollow fibers 32.

The hydrophobic porous hollow fiber 28 is formed of, for example, polypropylene, polyethylene, or polyvinylidene fluoride. Since the porous hollow fiber 28 is hydrophobic, the micro pores on the surface of the hollow fiber 28 permit passing gases alone within the housing body 21 so as to release the gases to the outside of the housing body 21. The surface of the hydrophobic porous hollow fiber 28 should have a porosity of about 30 to 90%, preferably about 60 to 85%. Also, the pore diameter should be about 0.01 to 0.45 micron, preferably about 0.01 to 0.2 micron. In general, the outer diameter of the porous hollow fiber 28 may be in the range of from 0.1 mm to 1.5 mm, and the wall thickness thereof may range from 10 $\mu$m to 200 $\mu$m.

For preparing the hydrophilic or hydrophobic hollow fiber described above, it is also possible to apply a hydrophilic treatment or a hydrophobic treatment to the surface of a porous hollow fiber. For the hydrophilic treatment, it is possible to use, for example, Pluronic, which is a registered trademark of Wyandotte Chemical Inc., or a neutral surface active agent. On the other hand, it is possible to use, for example, a silicone oil for the hydrophobic treatment.

The gas within the housing body 21 floats on the transfusing liquid regardless of the posture of the transfusion filtering device 1 so as to contact the inner wall 29 of the housing body 21. As shown in FIG. 2, the hydrophobic hollow fibers 28 are equidistantly arranged along the inner wall 29 of the housing body 21. Also, the hydrophobic hollow fibers 28 are arranged over the entire region of the inner wall 29 in a manner to extend from the thick wall portion 27 positioned near the transfusing liquid inlet port 23 to reach a region near the sealing member 31. It follows that the air bubbles staying within the housing body 21 are brought into contact with the hydrophobic hollow fibers 28 regardless of the posture of the transfusion filtering device 1. As a result, the air bubbles are released through the hydrophobic hollow fibers 28 to the outside of the housing body 21.

On the other hand, the hydrophilic hollow fibers 32 are arranged in the central portion of the housing body 21 in the axial direction of the housing body 21. Naturally, the air bubbles staying within the housing body 21 are not brought into contact with the hydrophilic hollow fibers 32, with the result that the filtering area of the hollow fiber 32 is not diminished by the presence of the air bubbles. It follows that the transfusion filtering device can be used in any optional posture. For example, the transfusion filtering device can be mounted to the arm of a patient without impairing the air releasing effect. Of course, the restriction imposed on the movement of the patient can be lessened.

At the beginning of the filtering operation, a transfusing liquid is poured into the first chamber 25. With increase in the amount of the transfusing liquid poured into the first chamber 25, the air within the housing body 21 is discharged through the hydrophobic hollow fibers 28 to the outside. This makes it unnecessary to conduct the air releasing operation of overturning the transfusion filtering device which is conducted in the conventional transfusion filtering device in preparation for the filtering operation. Needless to say, the air releasing effect can be further improved, if the distance between the adjacent hydrophobic hollow fibers 28 is shortened so as to increase the number of hydrophobic hollow fibers arranged within the housing body 21.

As shown in FIG. 1, the inner diameter of the second chamber 26 is aligned with the open portion of the hydrophilic hollow fibers 32 fixed to the sealing member 31. The particular construction permits suppressing the stay of the air bubbles within the second chamber 26.

In the transfusion filtering device 1 of the present invention, which is shown in the accompanying drawings, the housing body 21 is cylindrical. Also, the porous hollow fibers having a circular cross sectional shape are arranged within the housing body 21 such that the hollow fibers extend in the axial direction of the housing body 21. It follows that the hollow fibers can be arranged within the housing body with a high density. In other words, the transfusion filtering device can be formed compact while ensuring a sufficiently large surface area, which performs the filtering function, of the hollow fibers.

Figure 5:
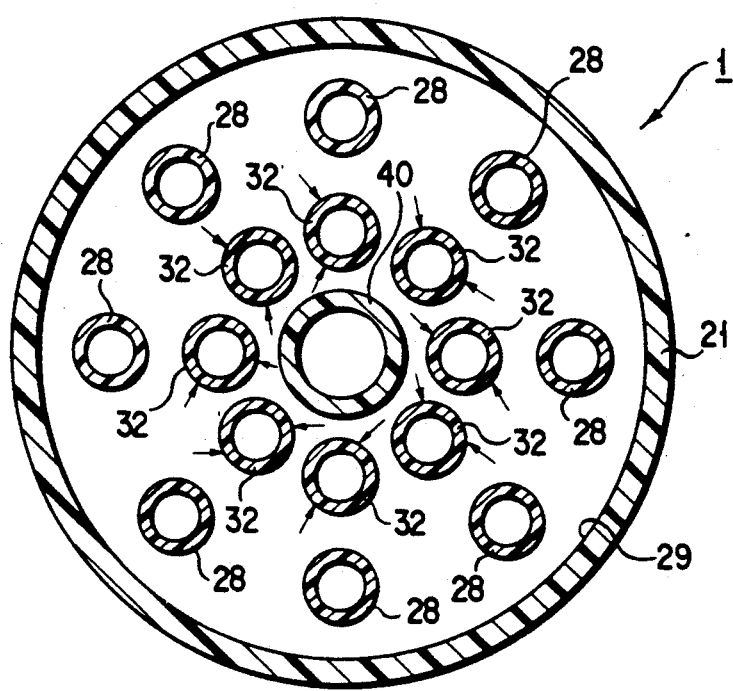
FIG. 5 is a cross sectional view along the line IV—IV shown in FIG. 4.

FIGS. 4 and 5 show another embodiment according to the present invention. This embodiment is featured in that the operation of overturning a transfusion filter for purging air during a priming operation can be dispensed with. The transfusion filtering device shown in FIGS. 4 and 5 is almost the same as that of the embodiment shown in FIGS. 1 and 2 except that an introducing member 40 is connected to the transfusing liquid inlet port 23 so as to extend downward in substantially coaxial with the housing 2, the lower end of the introducing member 40 being disposed near the bottom of the housing 2. Therefore, the same parts or members as those shown in FIGS. 1 and 2 are designated by the same reference numerals thereby omitting the explanations thereof. The shape of introducing member is preferably cylindrical, such as pipe and is preferably formed integrally with the inlet port 23.

This introducing member 40 has its lower end closed, and is provided around the lower wall thereof with a plurality of side openings 41, so that a transfusing liquid which is introduced from the inlet port 23 can be discharged via the side openings 41 into the interior of the housing 2. The transfusing liquid may be discharged from the lower end of the introducing member 40 instead of the side openings 41 if desired. The material for the introducing member 40 is preferably the same as that of the housing body 21. The housing body 21 is integrally formed with the inlet port 23. For the easiness of fabrication, the housing body 21 and the inlet port 23 may be separately prepared in advance and combined together by means of a lid (not shown).

In the embodiment shown in FIGS. 4 and 5, a transfusing liquid is introduced from the transfusing liquid inlet port 23, and then passed through the introducing member 40 to the side openings 41 to be discharged therefrom into the interior of the housing 2. The transfusing liquid discharged from the side openings 41 is accumulated in the housing 2 so that the housing 2 is gradually filled with the transfusing liquid from the bottom thereof. The transfusing liquid being gradually accumulated is simultaneously penetrated into the hydrophilic hollow fibers 32 through the wall thereof. Meanwhile, the air remaining at this moment in the hydrophilic hollow fibers 32 is gradually removed from the hydrophilic hollow fibers 32 through the dry portion of the wall of the hollow fibers 32. The air thus removed from the hydrophilic hollow fibers 32 is finally discharged out of the housing 2 via the hydrophobic fibers 28.

As described above in detail, the present invention provides a compact transfusion filtering device device capable of performing a sufficiently high filtering function. The transfusion filtering device of the present invention can be easily mounted to, for example, the arm of a patient for the transfusing purpose. What should also be noted is that, at the beginning of the filtering operation, the gas within the transfusion filtering device is discharged to the outside through the hydrophobic hollow fibers in accordance with pouring of the transfusing liquid into the filter. It follows that it is possible to omit the air releasing operation of overturning the transfusion filtering device before the filtering operation which is required in the conventional transfusion filter.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A compact transfusion filtering device, comprising:
a cylindrical housing having an inlet port for a transfusing liquid, said inlet port being positioned at an upper end portion of said cylindrical housing, and an outlet port for said transfusing liquid, said outlet port being positioned at a lower end portion of said cylindrical housing; and
air bubble removing means for removing from said cylindrical housing a plurality of air bubbles in said transfusing liquid that form on an inner wall of said cylindrical housing;
said air bubble removing means including a filtering portion provided within said housing, said filtering portion being positioned between said inlet port and said outlet port, said filtering portion including:
a plurality of hydrophilic porous hollow fibers arranged in a central portion of said housing, in an axial direction of said cylindrical housing; and
a plurality of hydrophobic porous hollow fibers arranged a predetermined distance apart from each other along said inner wall of said cylindrical housing adjacent to said plurality of air bubbles, said plurality of hydrophilic fibers surrounding said hydrophilic porous hollow fibers;
each of said hydrophobic porous hollow fibers extending from a shoulder portion around said inlet port of said cylindrical housing into a lower portion of said cylindrical housing so as to allow any of said plurality of air bubbles that come into contact with said plurality of hydrophobic porous hollow fibers to communicate with an atmospheric pressure through said shoulder portion of said cylindrical housing.

2. The transfusion filtering device according to claim 1, wherein said hydrophilic porous hollow fibers are bundled into a plurality of bundles, and said plurality bundles are arranged at a predetermined distance apart from each other in the central portion of said cylindrical housing.

3. The transfusion filtering device according to claim 1, wherein said hydrophobic porous hollow fibers are bundled into a plurality of bundles, and said plurality of bundles are arranged at a predetermined distance apart from each other along said inner wall of said cylindrical housing.

4. The transfusion filtering device according to claim 1, wherein said hydrophilic porous hollow fibers are respectively sealed at an end portion thereof at an upstream side of said cylindrical housing.

5. The transfusion filtering device according to claim 1, wherein said hydrophobic porous hollow fibers are respectively sealed at an end portion thereof at a downstream side of said cylindrical housing.

6. The transfusion filtering device according to claim 1, further comprising:
an introducing tube having a closed lower end portion disposed in said central portion of said cylindrical housing such that an upper portion of said introducing tue is connected to said inlet port, and a lower end portion of said introducing tube is disposed near a lower portion of said cylindrical housing, said introducing tube being provided at said lower wall portion thereof with an opening; and wherein:
said hydrophilic porous hollow fibers are arranged around said introducing tube.

7. A transfusion filtering device, comprising:
a cylindrical housing having an inlet port for a transfusing liquid, said inlet port being positioned at an upper end portion of said cylindrical housing, and an outlet port for said transfusing liquid, said outlet port being positioned at a lower end portion of said cylindrical housing;
a filtering portion provided within said cylindrical housing, said filtering portion being positioned between said inlet port and said outlet port; and
an introducing tube having a closed lower end portion disposed in a central portion of said cylindrical housing such that an upper end portion of said introducing tube is connected to said inlet port and said closed lower end portion of said introducing tube is disposed near said lower end portion of said cylindrical housing, said introducing tube being provided at a lower wall portion thereof with an opening;
air bubble removing means for removing from said housing a plurality of air bubbles that form on an inner wall of said cylindrical housing, said air bubble removing means including said filtering portion, said filtering portion comprising:
a plurality of hydrophilic porous hollow fibers arranged around said introducing tube in an axial direction of said cylindrical housing; and
a plurality of hydrophobic porous fibers, respectively extending from a shoulder portion around said inlet port of said cylindrical housing into said lower end portion of said cylindrical housing so as to enable said plurality of hydrophobic porous hollow fibers to communicate with an atmospheric pressure through said shoulder portion.

8. A transfusion filtering device according to claim 7, wherein said plurality of hydrophobic porous hollow fibers are bundled into a plurality of bundles, and said plurality of bundles are arranged at a predetermined distance apart from each other along said inner wall of said cylindrical housing adjacent said plurality of air bubbles for removing from said cylindrical housing any of said plurality of air bubbles that come into contact with said plurality of hydrophobic porous hollow fibers.

9. A transfusion filtering device according to claim 7, wherein each of said hydrophilic porous hollow fibers is respectively sealed at an end portion thereof at an upstream side of said cylindrical housing.

10. A transfusion filtering device according to claim 7, wherein each of said hydrophobic porous hollow fibers is respectively sealed at an end portion thereof at a downstream side of said cylindrical housing.

11. A transfusion filtering device according to claim 7, wherein said hydrophobic porous hollow fibers are bundled into a plurality of bundles, and said plurality of bundles are arranged at a predetermined distance apart from each other in said central portion of said cylindrical housing.

* * * * *

UNITED STATES PATENT AND TRADEMARK OFFICE
CERTIFICATE OF CORRECTION

PATENT NO. : 5,221,474

DATED : June 22, 1993

INVENTOR(S) : Osamu YOKONO et al

It is certified that error appears in the above-identified patent and that said Letters Patent is hereby corrected as shown below:

Title Page, item [56] References cited, under the "U.S. PATENT DOCUMENTS", "Croni" should read --Cronin--.

Signed and Sealed this

Sixth Day of September, 1994

*Attest:*

BRUCE LEHMAN

*Attesting Officer*     *Commissioner of Patents and Trademarks*